(12) United States Patent
Aguilar-Cordova (10) Patent No.: US 10,350,275 B2
(45) Date of Patent: Jul. 16, 2019

(54) METHODS OF CYTOTOXIC GENE THERAPY TO TREAT TUMORS

(71) Applicant: Carlos Estuardo Aguilar-Cordova, Waban, MA (US)

(72) Inventor: Carlos Estuardo Aguilar-Cordova, Waban, MA (US)

(73) Assignee: Advantagene, Inc., Auburndale, MA (US)

( * ) Notice: Subject to any disclaimer, the term of this patent is extended or adjusted under 35 U.S.C. 154(b) by 0 days.

(21) Appl. No.: 14/490,940

(22) Filed: Sep. 19, 2014

(65) Prior Publication Data

US 2015/0086541 A1    Mar. 26, 2015

Related U.S. Application Data

(60) Provisional application No. 61/880,864, filed on Sep. 21, 2013.

(51) Int. Cl.
*A01N 63/00* (2006.01)
*A61K 38/45* (2006.01)
*A61K 31/522* (2006.01)
*A61K 38/19* (2006.01)
*A61K 38/50* (2006.01)
*C07K 16/28* (2006.01)

(52) U.S. Cl.
CPC ............ *A61K 38/45* (2013.01); *A61K 31/522* (2013.01); *A61K 38/19* (2013.01); *A61K 38/50* (2013.01); *C07K 16/2818* (2013.01); *C12Y 207/01021* (2013.01); *C12Y 305/04001* (2013.01); *C12N 2710/10343* (2013.01)

(58) Field of Classification Search
USPC ........................................................ 424/93.2
See application file for complete search history.

(56) References Cited

U.S. PATENT DOCUMENTS

| | | | | |
|---|---|---|---|---|
| 6,372,208 B1 * | 4/2002 | Wilson | ............. | A61K 39/39541 424/93.2 |
| 8,119,129 B2 * | 2/2012 | Jure-Kunkel | ........ | A61K 31/505 424/130.1 |
| 8,318,916 B2 * | 11/2012 | Korman | ............. | A01K 67/0275 536/23.1 |
| 8,980,864 B2 * | 3/2015 | Hoge | .................... | C07K 14/705 514/44 R |
| 2015/0202290 A1 * | 7/2015 | Vanderwalde | ....... | C07K 14/535 424/142.1 |

FOREIGN PATENT DOCUMENTS

| | | | |
|---|---|---|---|
| EP | 3293201 | * | 3/2018 |
| WO | WO 2007/123737 | * | 11/2007 |
| WO | WO 2010/072900 | * | 7/2010 |
| WO | WO 2012/038606 | * | 3/2012 |
| WO | WO 2013/027988 | * | 2/2013 |

OTHER PUBLICATIONS

Elshami (Annals of Surg., Sep. 1995, vol. 222, No. 3, p. 298-310).*
Zou (Nat Rev Immunol, 2008, 8, 467-477).*
Chen (Clin Cancer Res, Dec. 15, 2012, vol. 18, No. 24, p. 6580-6587).*
Tabernero (Am Soc Clin Oncol Meeting May 31-Jun. 4, 2013; Abstract 3622) 3.*
Mellman (Nature, Dec. 2011, vol. 480, p. 480-489).*
Feltner (Drug Forecast, 2012, vol. 37, No. 9, pp. 503-530).*
Ram (Nature Med., Dec. 1997, vol. 3, No. 12, p. 1354-1361).*
Wang (Human gene therapy, Jan. 20, 2003, vol. 14, No. 2, pp. 117-127).*
Sandmair (Human Gene Therapy, Nov. 1, 2000, vol. 11, No. 6, p. 2197-2205).*
Immonen (Mol. Therapy, Nov. 2004, vol. 10, No. 5, p. 967-972).*
Yi (Current Gene Therapy, 2011, vol. 11, p. 218-228).*
Palu (Gene Therapy, 1999, vol. 6, p. 330-337).*
van Elsas (J. Exp. Med., Aug. 2, 1999, vol. 190, No. 3, p. 355-366).*
Pardoll (Nature Reviews, Apr. 2012, vol. 12, p. 252-264).*
Manno (Nature Medicine, 2006, vol. 12, p. 342-347.*
Guo (Adv Cancer Res., published online Jul. 2013, vol. 119, p. 421-475).*
Vanneman ("Combining immunotherapy and targeted therapies in cancer treatment", Nature Reviews, Apr. 2012, vol. 12, p. 237-251).*
Aguilar (J. Cell. Biochem., 2011, vol. 112, p. 1969-1977).*
Pardoll (J. Exp. Med., 2012, vol. 209, No. 2, p. 201-209).*
Ngiow (Cancer Res., 2011, vol. 71, No. 21, p. 6567-6571).*
Bartkowiak, D. et al. (2013) "Radiotherapy in the Management of Prostate Cancer After Radical Prostatectomy," Future Oncol. 9(5):669-679.
Cao, Y. et al. (2012) "Tim-3 Expression in Cervical Cancer Promotes Tumor Metastasis," PLoS One, 8(1):e53834.
ClinicalTrials.gov. (Apr. 12, 2008) Bethesda, MD: National Library of Medicine (US). Identifier NCT00658892, "Monoclonal Antibody Therapy in Treating Patients with Stage IV Melanoma."
Goding, S. et al. (2013) "Restoring Immune Function of Tumor-Specific CD4+ Cells During Recurrence of Melanoma," J Immunol, 190(9):4899-4909.
Goldberg, M. V. (2011) "LAG-3 in Cancer Immunotherapy," Curr Top Microbiol Immunol, 344:269-278.
King, C. R. (2013) (Adjuvant Versus Salvage Radiotherapy for High-Risk Prostate Cancer Patients, Semin Radiat Oncol, 23:215-221.
Lo, S. S. et al. (2013) "Review: What is the Most Appropriate Clinical Target Volume for Glioblastoma?" SNC Oncol. 2(5):419-425.
Manno, C. S. et al. (2006) "Successful Transduction of Liver in Haemophilia by AAV-Factor IX and Limitations Imposed by the Host Immune Response," Nature Med, 12(3):342-347.

(Continued)

*Primary Examiner* — Michael C Wilson
(74) *Attorney, Agent, or Firm* — Ann-Louise Kerner; Lathrope Gage LLP (57) ABSTRACT

A method is disclosed for decreasing or retarding an increase in the size of a localized or metastatic tumor by using a combination of an immune stimulating cytotoxic gene therapy and immune-checkpoint modulating agent, in conjunction with other therapies, including radiation therapy, chemotherapy, surgery, and immunotherapies.

6 Claims, 3 Drawing Sheets

(56) References Cited

OTHER PUBLICATIONS

Mingozzi, F. et al. (2007) "Immune Responses to AAV in Clinical Trials," Current Gene Therapy, 7:316-324.
Mueller, J. L. et al. (2013) "Quantitative Segmentation of Fluorescence Microscopy Images of Heterogeneous Tissue: Application to the Detection of Residual Disease in Tumor Margins," PLoS One 8(6):e66198.
Ngiow, S. F. et al. (2011) "Anti-TIM3 Antibody Promotes T Cell IFN-δ-Mediated Antitumor Immunity and Suppresses Established Tumors," Cancer Res, 71(10):3540-3551.
Ngiow, S. F. et al. (2011) "Prospects for TIM-Targeted Antitumor Immunotherapy," Cancer Res, 71(21):6567-6571.
Okudaira, K. et al. (2009) "Blockade of B7-H1 or B7-DC Induces an Anti-Tumor Effect in a Mouse Pancreatic Cancer Model," Int J of Onc, 35(4):741-749.
Pardoll, D. M. (2012) "The Blockade of Immune Checkpoints in Cancer Immunotherapy," Nature Reviews, 12:252-264.
Piao, Y. et al. (2013) "Prognostic Value of T Cell Immunoglobulin Mucin-3 in Prostate Cancer," Asian Pacific J Cancer Prev, 14(6):3897-3901.
Podojil, J. R. et al. (2012) "Targeting the B7 Family of Co-Stimulatory Molecules: Successes and Challenges," BioDrugs, 27(1):1-13.
Schaverien, M. V. et al. (2013) "Use of Boost Radiotherapy in Oncoplastic Breast-Conserving Surgery—A Systematic Review," EJSO 39:1179-1185.
Shin, T. et al. (2005) "In vivo Costimulatory Role of B7-DC in Tuning T Helper Cell 1 and Cytotoxic T Lymphocyte Responses," J Exp Med, 201(10):1531-1541.
Thompson, I. M. et al. (2013) "Adjuvant and Salvage Radiotherapy After Prostatectomy: AUA/ASTRO Guideline," J Urol, 190:441-449.
Topalain, S. L. et al. (2011) "Targeting the PD-1/B7-H1(PD-L1) Pathway to Activate Anti-Tumor Immunity," Curr Opin Immunol, 24(2):207-212.
Woo, S. et al. (2012) "Immune Inhibitory Molecules LAG-3 and Pd-1 Synergistically Regulate T Cell Function to Promote Tumoral Immune Escape," Cancer Res, 72(4):917-927.
Yan, J. et al. (2013) "Tim-3 Expression Defines Regulatory T Cells in Human Tumors," PLoS One, 8(3):e58006.

* cited by examiner

Figure 1:
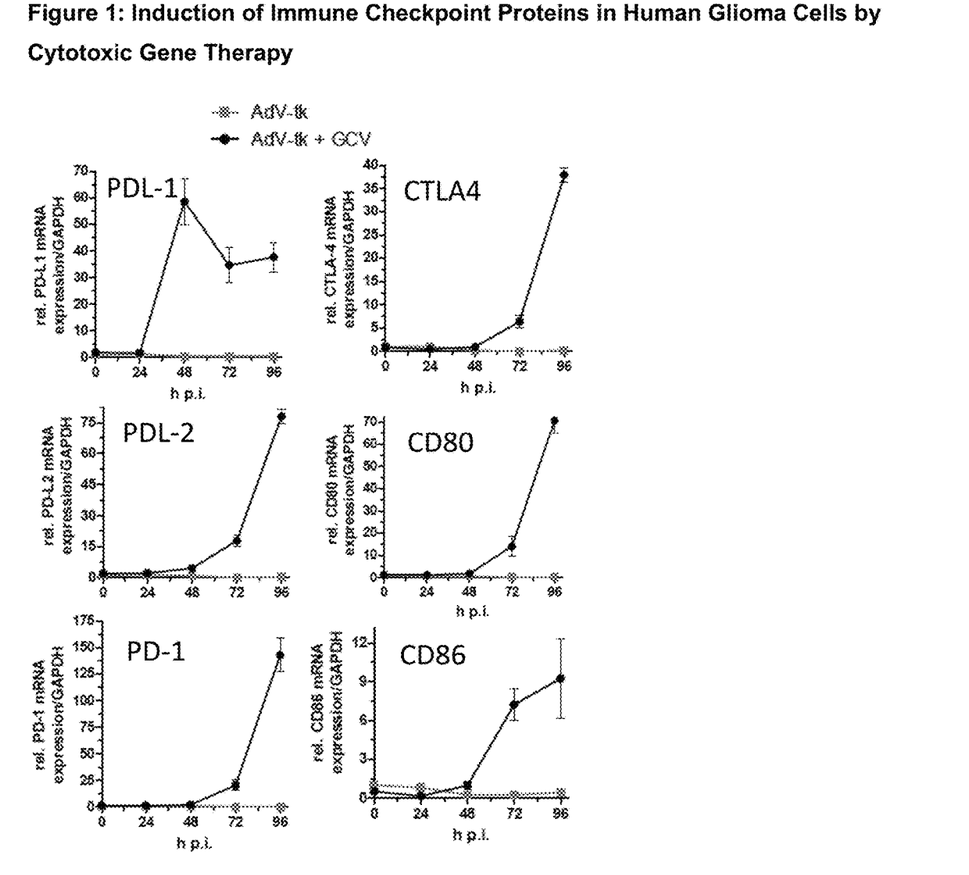

Figure 1: Induction of Immune Checkpoint Proteins in Human Glioma Cells by Cytotoxic Gene Therapy Figure 2 Induction of Immune Checkpoint Proteins in Murine Glioma Cells by Cytotoxic Gene Therapy Figure 3: Induction of PD-L1 expression in tumors from pancreatic cancer patients treated with AdV-tk/prodrug

METHODS OF CYTOTOXIC GENE THERAPY TO TREAT TUMORS

REFERENCE TO RELATED APPLICATIONS

This application claims the benefit and priority of U.S. Provisional Application No. 61/880,864 filed Sep. 21, 2013, the content of which are incorporated herein

FIELD OF THE INVENTION

The present invention is directed to a method for the treatment of tumors using immune stimulating cytotoxic gene therapy in combination with immune-checkpoint modulating agents.

DESCRIPTION OF RELATED ART

In one embodiment of the present invention, an approach which combines a course or courses of an immune stimulating cytotoxic gene therapy, such as an adenoviral vector expressing the Herpes simplex virus thymidine kinase gene administered in conjunction with an anti-herpetic prodrug, with a monoclonal antibody with specific affinity for an immune checkpoint protein, such as the PD-1 protein, used either in parallel or sequentially for the treatment of a tumor, such as pancreatic cancer.

In another embodiment of the present invention, a therapeutic approach which combines a course a the immune stimulating cytotoxic gene therapy, such as an adenoviral vector expressing Herpes simplex virus thymidine kinase gene administered in conjunction with an anti-herpetic prodrug, with a monoclonal antibody with specific affinity for another immune checkpoint protein, such as the CTLA-4 protein, used either in parallel or sequentially in the treatment of a tumor, such as malignant melanoma.

BACKGROUND OF THE INVENTION

The Prevalence of Cancer

Cancer affects millions of people. Cancer is the second leading cause of death and accounts for one-fifth of the total mortality in the United States. There are many different types, primary and metastatic and the following are some of the predicted morbidities and mortalities in the USA (R. Siegel, J. Ma, Z. Zou, A. Jemal, C A Cancer J. Clin. 64:9-29, 2014).

In 2014 there will be an estimated 1,665,540 new cancer cases. It is estimated that there will be 855,220 new male cases, and 810,320 new female cases. There will be 338,450 genital tumors (uterine cervix, uterine corpus, ovary, vulva, vagina, prostate, testis, and others) 298,610 digestive tumors (esophagus, stomach, small intestine, colon, rectum, anus, pancreas, liver, and others), 235,030 newly diagnosed breast cancers. Other tumors that comprise the rest of newly diagnosed cancers include, urinary system (141,610), lymphoma (79,990) respiratory system (242,550), brain and other nervous system (23,380), skin (81,220). Nonsolid tumors (leukemia) only account for 52,380 of the newly diagnosed tumors.

It is estimated that there will be 586,000 deaths in the USA due to cancer in 2014 (310,000 male, and 276,000 female). In the female population it is estimated that there will be 62,290 from the digestive system, 73,000 from the respiratory system (mostly lung) 40,000 from breast cancer, and other solid tumor sites comprising the rest of the 276,000. Nonsolid tumors will account for approximately 10,000 cancer deaths in females. In the male it is estimated that there will be 85,000 deaths from digestive tumors, 90,000 from the respiratory system (mostly lung), 29,000 from prostate cancer, and other tumor sites comprising the rest of the 310,000 cases. In males, only 14,000 of the estimated cancer deaths are from nonsolid tumors.

A majority of the deaths from cancer are due to the systemic metastatic effects of the disease. Metastatic disease is the growth of tumor cells outside of their site of origin. It is not uncommon for some cancer patients to have undetected metastasis at the time of original diagnosis, these are sometime referred to as micrometastasis.

Current Therapies

Cancer is characterized by the uncontrolled division of a population of cells. This uncontrolled division typically leads to the formation of a tumor, which may subsequently metastasize to other sites.

The current therapies for cancer can be divided into four categories: surgery, radiation, chemotherapy, and immunotherapy.

Surgical oncology can be further divided into three distinct areas: curative, debulking, and palliative. The principal goal of surgery is to completely remove the tumor and obtain "clear" surgical margins. It is often not possible to completely resect the tumor because of location or because of local invasion into surrounding normal tissues. Examples of these are tumors that have invaded locally into nerve roots, muscle or bone. Surgery is the only therapy required for tumors that are diagnosed at an early stage that have not metastasized via the blood stream or the lymphatics, or invaded sensitive or inaccessible tissues. Although even in those situations additional therapy may be indicated. For example, women who undergo lumpectomies often receive a course of radiation after their surgery to prevent recurrence. A thorough staging evaluation is required before the patient is deemed probably curable by surgery alone. This staging work-up is performed to show that there is no spread of disease. Even after this many patients recur after what is deemed complete tumor resection. Surgery is also used as a debulking procedure where by the tumor has been or will be further inhibited by chemotherapy, radiotherapy or both chemotherapy and radiation therapy. The reason for performing radiation and chemotherapy first is because the tumor may initially be too large to remove and must be shrunk before clear surgical margins can be obtained. The other role that surgery plays is palliation (relief of symptoms). In this sense it is not used with curative intent but is only offered to relieve symptoms. A case of palliative oncologic surgery is the patient that has disease compressing the spinal cord and the tumor is removed to relieve the symptoms of pain and neurological deficit. In short surgery treats cancer by removing it.

Radiation therapy is used in approximately 50% of the patients that have cancer. Radiation therapy is used with curative, adjuvant or palliative intent. There are certain cancers that can be cured by radiation therapy alone. The group of patients judged to be able to benefit from radiation monotherapy are those that have been fully staged and are found to have local or local or loco-regional disease. Analogous to the way the surgeon uses the scalpel, the radiation oncologist uses the radiation beam to destroy cancer cells by causing physical damage, such as double strand breaks in the DNA of the cell. The radiation can be generated in high doses, low doses, short term or long term. The sources can be radioactive seeds, radioactive source probes or external beams such as the high energy x-rays that are produced by a machine called a linear accelerator. Cancers that, in some situations, be can be cured by radiation alone include prostate cancer, head and neck cancer, cervical cancer, brain tumors and other cancers. However, as in all other cancer therapy modalities, there are many patients that recur.

Most often radiation therapy is used in an adjuvant setting. The radiation is given either before or after surgery or chemotherapy. Examples of these include the patient with breast cancer that is given radiation after lumpectomy; or the patient that has head and neck cancer that has been surgically removed and is at high risk for local recurrence; or a patient that does not have clear surgical margins. This same type of interaction can occur with chemotherapy. For example, when a tumor has been shrunk by chemotherapy and radiation is given to eradicate remaining tumor cells not destroyed by the chemotherapy, or when radiation and chemotherapy are mutually sensitizing, such as with 5-fluorouracil.

The other way that radiation therapy is used is in the palliative setting where it can relieve symptoms of bone pain or neurological symptoms related to the brain or spinal cord compression.

Chemotherapy works by interfering with different phases of the cell cycle or intercalating with the DNA of the cancer cell. As with other modalities, it is used with curative intent, in the adjuvant setting, concomitantly with radiation, or it can be used palliatively. The regimen of chemotherapy that is used is dependent on the disease site and pathological subtype. Chemotherapy is given systemically and acts on cancer cells throughout the body. This systemic effect is unlike radiation and surgery that only destroy the cancer cells at the site of therapy. Chemotherapeutic agents are most often given as multi-drug regimens in order to take advantage of the different mechanisms of action of each drug and to avoid single drug-resistant mutant-cell proliferation.

Chemotherapy has shown good curative outcomes in patients with testicular tumors and lymphomas. More commonly, chemotherapy is given in the adjuvant setting in combination with surgery, radiation, or both. For example, chemotherapy is given prior to radiation in patients with non-small cell lung cancer, bladder cancer, head and neck cancer and Hodgkin's lymphoma. It is given concomitantly with radiation for patients small cell lung cancer, anal carcinoma, most gastro-intestinal malignancies, (stomach, rectum, esophogous, pancreas). It is given after surgery for bladder cancer, pancreatic cancer, stomach cancer, breast cancer and other solid tumors. It is used as a palliative agent for the patients that have pain or neurological symptoms.

Limitations of Current Therapies

The standard therapies above have significant limitations. None are 100% curative and all have associated toxicities. Surgery and radiation have the limitation that they can only treat locally or loco-regional disease. There is also a dose limit to the amount of radiation that can be given before there is too much damage to normal neighboring structures. Similarly, there is a limit to how much a surgeon may remove in order to get a clear surgical margin. Removal of too much normal tissue can cause excessive morbidity to the patient. Chemotherapy affects all tissues of the body since it is given systemically. Different chemo-therapeutic agents affect different organs differently. The most commonly affected organ is the bone marrow, where the drop in blood counts limits the dose of chemotherapy that can be given to the patient. But there can also be significant toxicity to kidneys, liver, gastrointestinal tract, and other tissues.

Primary solid tumors are generally treated by surgical resection. However, the majority of patients who have solid tumors also possess micrometastases beyond the primary tumor site. If treated with surgery alone, approximately 70% of these patients will experience recurrence of the cancer. Therefore, in addition to surgery, many cancers are also treated with a combination of therapies involving cytotoxic chemotherapeutic drugs (e.g., vincristine, vinblastine, cisplatin, methotrexate, 5-FU, etc.) and/or radiation therapy. One difficulty with this approach, however, is that radiotherapeutic and chemotherapeutic agents are toxic to normal tissues, and often create life-threatening side effects. In addition, these approaches often have extremely high failure/remission rates (up to 90% depending upon the type of cancer).

Developing Therapies

In addition to surgery, chemo- and radiation therapies, many have attempted to bolster or augment an individual's own immune system in order to eliminate the cancer cells. Historically, several immunotherapies have utilized bacterial or viral components as adjuvants, in order to stimulate the immune system to destroy the tumor cells. Examples of such components include BCG, endotoxin, mixed bacterial vaccines, interferons (alpha, beta, and gamma), interferon inducers (e.g., *Brucella abortus*, and various viruses), and thymic factors (e.g., thymosin fraction 5, and thymosin alpha-1) (see generally "Principles of Cancer Biotherapy," Oldham (ed.), Raven Press, New York, 1987). Such agents have generally been useful as adjuvants and as nonspecific stimulants in animal tumor models, but have not yet proved to be generally effective in humans.

Lymphokines have also been utilized in the treatment of cancer. Briefly, lymphokines are secreted by a variety of cells, and generally have an effect on specific cells in the generation of an immune response. Examples of lymphokines include TNF-alpha, interferons, interleukins (e.g. IL-1, -2, -3, -4, and -12 as well as colony stimulating factors such as G-CSF, GM-CSF, and M-CSF). One group has utilized IL-2 to stimulate peripheral blood cells in order to expand and produce large quantities of cells that are cytotoxic to tumor cells (Rosenberg et al., N. Engl. J Med. 313:1485-1492, 1985). Another group of agents being studied are called chemokines. These are agents that attract immune cells to a site and thus may stimulate an immune response. An example of these is Rantes.

Others have suggested the use of antibody-mediated anticancer therapies. Briefly, antibodies may be developed which recognize certain cell surface antigens that are either unique, or more prevalent on cancer cells compared to normal cells. These antibodies, or "magic bullets," may be utilized either alone or conjugated with a toxin in order to specifically target and kill tumor cells, or to block the function of the target protein (Dillman, "Antibody Therapy," Principles of Cancer Biotherapy, Oldham (ed.), Raven Press, Ltd., New York, 1987). For example, Ball et al. (Blood 62:1203-1210, 1983) treated several patients with acute myelogenous leukemia with one or more of several monoclonal antibodies specific for the leukemia, resulting in a marked decrease in circulating leukemia cells during treatment. Similarly, others have utilized toxin-conjugated antibodies therapeutically to treat a variety of tumors, including, for example, melanomas, colorectal carcinomas, prostate carcinomas, breast carcinomas, and lung carcinomas (see Dillman, supra). More recently, mononclonal antibodies targeting a wide range of have been demonstrated to be effective, and many have been approved for the treatment of a wide range of tumor types (J. M. Reichert, V. E. Valge-Archer, Nat Rev Drug Disc, 6(5):349-355, 2007).

Immune Checkpoint Proteins as Therapeutic Targets

Recent progress in cancer treatment has been made by targeting Immune checkpoint proteins with monoclonal antibodies. Immune checkpoint proteins are regulatory components of the immune system. It is thought that immune checkpoint proteins modulate the intensity and duration of the immune responses, and have key functions in limiting excessive inflammation and the prevention of autoimmunity. It has been observed that many tumor types co-opt the immune checkpoint regulatory scheme as a means to evade antitumor immune surveillance. The blockade of a number of immune checkpoint proteins has been demonstrated to be an effective approach in the treatment of cancer. Ipilimumab (anti-CTLA-4) has been approved as a treatment for of metastatic melanoma, including patients with brain metastases (K. Margolin, Oncoimmunology 1:1197-1199, 2012; F. S. Hodi, et al Nature Clinical Practice, 5, 557-561,2008). CTLA-4 is expressed on activated T cells and is thought to act by limiting T cell activation by competing with CD28 coactivator protein in binding with CD80/CD86 ligands (D. Pardoll, C. Drake, J Exp Med, 209: 201-209). Programmed cell Death 1 (PD-1) is another checkpoint protein that is expressed on T cells, B cells and NK cells. Studies targeting PD-1 and PD-L1 have reported clinical responses in a variety of tumor types with favorable safety profiles (J. R. Brahmer et al N Engl J Med 366: 2455-2465. 2012; S. L. Topalian N Engl J Med 366:2443-2454).

Monotherapy treatment of tumors with an Immune checkpoint inhibitor antibody, such as Anti-CTLA-4, is known to provide a clinically meaningful but relatively modest increase in overall survival, and complete and partial responses only occurred in a small subset of subjects (about 10.9%) (Senzer et al, J Clin Oncol. 27(34):5763-5771, 2009). Antibodies targeting other checkpoints, such as PD-1 also have shown clinical efficacy with durable responses in a number of tumor types, but response rates remain suboptimal with less than 50% of patients responding (J. R. Brahmer et al N Engl J Med 366: 2455-2465. 2012; S. L. Topalian N Engl J Med 366:2443-2454). There is a need to improve response rates for antibodies targeting checkpoint inhibitors, such as CTLA4, PD-1, and PD-L1.

Oncolytic Viruses as Oncology Therapeutics

Recent progress has also been made in the use of oncolytic viruses applied to the treatment. Oncolytics virus refers to a virus capable of selectively replicating in and slowing the growth or inducing the death of cancerous or hyperproliferative cells, while having minimal effects on normal cells. Examples of oncolytic viruses, and viruses from which oncolytic virus have been derived include, vesicular stomatitis virus (VSV), Newcastle disease virus (NDV), herpes simples virus (HSV), reovirus, measles virus, retrovirus, influenza virus, Sinbis virus, vaccinia virus, adenovirus, or the like (e.g., Kirn et al, Nat Med 7:781(2001); Coffey et al., Science 282:1332 (1998); Lorence et al., Cancer Res. 54:6017 (1994); and Peng et al., Blood 98:2002 (2001)).

An example of an oncolytic virus is Talimogene laherparepvec, which is based on a HSV-1 [strain JS1] ICP34.5-/ICP47-/hGM-CSF. Talimogene laherparepvec is an intratumorally delivered oncolytic immunotherapy comprising an immune-enhanced HSV-1 that selectively replicates in solid tumors, and has been engineered to express the immune stimulatory cytokine GM-CSF (Lui et al., Gene Therapy, 10:292-303, 2003; U.S. Pat. No. 7,223,593 and U.S. Pat. No. 7,537,924).

Talimogene laherparepvec produces a direct oncolytic effect by replication of the virus in the tumor, and induction of an anti-tumor immune response enhanced by the local expression of GM-CSF. Since melanoma is a disseminated disease, this dual activity is beneficial as a therapeutic treatment. The intended clinical effects include the destruction of injected tumors, the destruction of local, locoregional, and distant uninjected tumors, a reduction in the development of new metastases, a reduction in the rate of overall progression and of the relapse rate following the treatment of initially present disease, and prolonged overall survival.

Talimogene laherparepvec has been tested for efficacy in a variety of in vitro (cell line) and in vivo murine tumor models and has been shown to eradicate tumors or substantially inhibit their growth at doses comparable to those used in clinical studies. Nonclinical evaluation has also confirmed that GM-CSF enhances the immune response generated, enhancing both injected and uninjected tumor responses, and that increased surface levels of MHC class I molecules result from the deletion of ICP47. Talimogene laherparepvec has been injected into normal and tumor-bearing mice to assess its safety. In general, the virus has been well tolerated, and doses up to $1 \times 10^8$ PFU/dose have given no indication of any safety concerns. (See, for example, Liu et al., Gene Ther 10: 292-303, 2003)

Clinical studies have been or are being conducted in several advanced tumor types (advanced solid tumors, melanoma, squamous cell cancer of the head and neck, and pancreatic cancer), with over 400 subjects treated with talimogene laherparepvec (see, for example, Hu et al., Clin Can Res 12: 6737-6747, 2006; Harrington et al., J Clin Oncol. 27(15a):abstract 6018, 2009; Kaufman et al., Ann Surgic Oncol. 17: 718-730, 2010; Kaufman and Bines, Future Oncol. 6(6): 941-949, 2010). Clinical data indicate that talimogene laherparepvec has the potential to provide overall clinical benefit to patients with advanced melanoma. In particular, a high rate of complete response was achieved in stage IIIc to IV melanoma (Scenzer et al., J. Clin. Oncol. 271(12):907-913, 2009). In addition, responses were observed in both injected and uninjected sites, including visceral sites.

While very promising activity of oncolytic viruses has been observed, This multistep mechanism requires the utilization of an oncolytic virus of a type that is able to infect and replicate efficiently within the cancerous or hyperproliferative cells that are being targeted. The activity of oncolytic viruses, such as the example of talimogene laherparepvec, depends on the lysis of cancerous or hyperproliferative cells in which they are able to replicate. Furthermore, during replication and spread of the oncolytic virus, the immune system may recognize such and agent, limiting the spread of virus particle locally between cells, and systemically between tumors or metastases or micrometastases. This could limit effectiveness of this approach.

Cancer Gene Therapy (Gene Delivery Vehicles)

Gene Delivery Vehicles (GDV) can be classified as two main types—viral and non-viral. Both types are reviewed in detail in Cell and Gene Therapy, N.S. Templeton Ed. CRC Press, 2008. The most commonly used viral systems are retroviral vectors and adenoviral vectors, in part for historical reasons and in part because they have been relatively straightforward to make in clinically useful quantities. These vectors have both been used extensively in the clinic, and some clinical trials have also been conducted using adeno-associated viral vectors, rhabdoviruses, herpes viral vectors and vectors based on vaccinia virus or poxviruses. These viruses have various strengths and weaknesses, but are all relatively efficient in delivering genes to target tissues. Limitations include difficulties in making sufficient quantities for some vectors, inability to accurately target the gene delivery in vivo, toxic or immunological side effects of viral gene products. However it should be noted that even with the relatively efficient viral vectors it is not reasonable at present to expect that a gene can be delivered to every sick cell, and so therapy need to be accomplished by means that are compatible with this issue.

Non viral systems include naked DNA, DNA formulated in liposomes and DNA formulated with polycation condensing agents or hybrid systems. These systems are more amenable to building in rational regulated steps to accomplish a long in vivo half-life, delivery to the target cell/tissue, entry into the cytoplasm and nucleus and then subsequent expression. Although there are possible solutions to each of these issues, they have not yet been efficiently combined, and efficiency of gene transfer in vivo remains an issue at this time. So for these systems also, it is not reasonable to expect to be able to deliver a gene to every cell, for example in a tumor.

Therefore, in cancer therapies using gene delivery vehicles, it is necessary to use mechanisms that allow some kind of amplification of the gene delivery events. These may include stimulation of the immune system, various forms of bystander effects, spread of apoptosis, anti-angiogenic effects, pro-coagulant effects, replication competent viral vectors or other mechanisms.

Some cytotoxic GDVs, such as AdV-tk utilize viral components. Both oncolytic viruses and viral cytotoxic GDVs have been investigated as therapeutic approaches for cancer. Key differences in the mechanism by which they function. Oncolytic viruses rely on viral replication for lysis for the target cancer cell. Cytotoxic GDVs such as AdV-tk and prodrug generate a cytotoxic effect by delivering a gene, the expression of which in or proximal to a cancer cell, results in a local cytotoxic effect independent of replication of the viral gene delivery vehicle.

Cancer Gene Therapy Methods

Because of the generally dismal outlook for many cancer patients and the plateau in improvements with conventional therapies such as those described above, there has been considerable interest in using novel modalities such as gene therapy for treatment of cancer (see F. Farzaneh, U. Trefzer, W. Sterry and P. Walden: "Gene therapy of Cancer" Immunology Today 19: 294-296, 1998). These include various paradigms such as: introduction of genes for various cytokines and chemokines in order to generally stimulate immunity against the tumor and its presumed tumor associated antigens (TAAs e. g. Addison et al. Gene Ther. 5: 1400-1409 1998); administration of genes for specific TAAs to stimulate immunity against these antigens (e. g. Schlom & Hodge Immunol Rev. 170: 73-84 1999); treatment with tumor suppressor or apoptosis inducing genes such as p53 (Eastham J A J. Urol. 164: 814-9 2000); treatment with genes the products of which can lead to suppression of angiogenesis or otherwise diminish blood-flow to tumor sites (e.g. Grischelli et al Proc Natl Acad Sci USA 95: 6367-6372 1998, WO 96/21416); treatment with genes the products of which will metabolize inactive compounds into active anti-tumor compounds (Connors, Gene Ther. 2: 702-709 1995, Deonarian et al. Gene Ther. 2: 235-244 1995); and combinations of these (e. g. Soler M N,); various other modalities such as those designed to potentiate T cell anti-tumor responses. The vectors used include retroviral vectors, adenoviral vectors, naked and formulated DNA, herpes viral vectors, adeno-associated vectors, and many other kinds of vectors (see T. Friemann 1999 op. cit.). Animal experiments have shown the possibility of success with some of these modalities and vectors and many of these continue to have promise. However, as noted above, there are logistical difficulties in implementing trials and putting into use many of these therapies. This has been exacerbated because gene therapy approaches have often been seen as monotherapies or used alone in patients with end-stage disease. The introduction and use of gene therapy approaches would be simpler if it were understood what their interactions with standard of care therapies were and it were used as an adjuvant therapy in all stages of disease.

A number of animal tumor studies have been performed with adenoviral vector encoding the Herpes virus thymidine kinase (HSVTK, AdTk, AdV-tk, etc) (L. K. Aguilar et al. J Cell Biochem. 112(8):1969-1977, 2011 and references therein). In addition replicating adenoviral vectors encoding TK (O. Wildner et al. Gene Therapy 6: 57-62 1999) and the use of adenoviral vectors encoding prodrug activating genes (PDAG) with radiation therapy (Freytag et al Hum. Gene Ther. 9: 1323-1333 1998 and references therein) have been reported in animal models. However implementation of these therapies in the clinic face considerable issues as described in this specification. In addition clinical trial results with an adenoviral vector encoding TK in conjunction with anti-herpetic prodrug has also been reported in patients suffering from a variety of cancers including prostate cancer (J. R. Herman, Hum. Gene Ther. 10:1239-1249 1999), malignant glioma (E. A. Chiocca et al, J Clin Oncol. 29(27):3611-9, 2011), and mesothelioma (D. H. Sterman et al, Clin Cancer Res 11(20):7444-53, 2005). While collectively these studies provide promising data, improvements in efficacy remain a need.

Problems in Introducing New Therapies

Clinical trials conducted in an ethical and legal manner follow established rules of conduct and practice (e.g. see the US Code of Federal Regulations—Chpt. 21). Such guidelines are enforced and policed by patient advocacy groups, the National Institute of Health, the ethical standards and advice of the physicians, by Institutional Review Boards set up to specifically review such issues in every trial conducted at the specific medical institution, and by the national drug approval agency (in the USA this is the Food and Drug Administration, FDA). Trials are therefore conducted in a manner that does not deprive a patient of the most appropriate treatment that would normally be used on that patient (the clinical standard of care). Therefore it is difficult to determine the efficacy of new therapies, especially in cancer, as stand-alone treatments for the disease. The only context where such therapies can be introduced clinically is when all other therapies have been tried, and no therapy is left that is expected to have a clinical benefit. Such patients usually have advanced disease with short life expectancy. This makes the testing of such new therapies very difficult and unlikely to yield positive results, given the advanced stage of disease. An alternative to this approach is to test candidate therapies that can be used in the context of current standard of care and simply be given in addition to current therapy. This demands that the new therapy at least does not negatively interact with current therapy and also vice versa. Ideally the new therapy would be expected to show collaborative effects with the current clinical treatment. In addition it is difficult and expensive during trials and also for new therapies if extra medical care such as infusions requiring hospitalization or extensive home care are required. Therefore any new therapy that adds a minimum of extra hospital care or extensive home care will be more acceptable to patients, physicians and those institutions paying for healthcare. This in turn will make these therapies more likely to go through to approval by healthcare authorities and be used by treating physicians.

The present technology is described herein using several definitions, as set forth throughout the specification. Unless otherwise stated, the singular forms "a," "an," and "the" include the plural reference. For example, a reference to "a virus" includes a plurality of virus particles, and a reference to "a nucleic acid" is a reference to one or more nucleic acids.

As used herein, the term "administration" of an agent or drug to a subject includes any route of introducing or delivering to a subject a compound to perform its intended function. Administration can be carried out by any suitable route, including orally, intratumorally, intracranially, parenterally (intravenously, intramuscularly, intraperitoneally, or subcutaneously), rectally, or topically. Administration includes self-administration and the administration by another.

As used herein, the term "antibody" means a polypeptide comprising a framework region from an immunoglobulin gene or fragments thereof that specifically binds and recognizes an antigen, e.g., a PD-1 polypeptide. Use of the term antibody is meant to include whole antibodies, including single-chain antibodies, and antigen-binding fragments thereof. The term "antibody" includes bispecific antibodies and multispecific antibodies so long as they exhibit the desired biological activity or function.

As used herein, the term "cancer" refers to a class of diseases of humans (and animals) characterized by uncontrolled cellular growth. As used herein, "cancer" is used interchangeably with the terms "tumor," "malignancy," "hyperproliferation" and "neoplasm(s)." The term "cancer cell(s)" is interchangeable with the terms "tumor cell(s)," "malignant cell(s)," "hyperproliferative cell(s)," and "neoplastic cell(s)" unless otherwise explicitly indicated. Similarly, the terms "hyperproliferative," "hyperplastic," "malignant" and "neoplastic" are used interchangeably, and refer to those cells in an abnormal state or condition characterized by rapid proliferation. Collectively, these terms are meant to include all types of hyperproliferative growth, hyperplastic growth, neoplastic growth, cancerous growths or oncogenic processes, metastatic tissues or malignantly transformed cells, tissues, or organs, irrespective of histopathologic type or stage of invasiveness.

As used herein, the term "chemotherapy" refers to any therapy that includes natural or synthetic chemotherapeutic agents now known or to be developed in the medical arts. Examples of chemotherapeutic agents include the numerous cancer drugs that are currently available. However, chemotherapy also includes any drug, natural or synthetic, that is intended to treat a disease state. In certain embodiments, chemotherapy may include the administration of several state of the art drugs intended to treat the disease state. Examples include chemotherapy with doxorubicin, cisplatin, 5-fluorouracil, fludarabine and bendamustine.

As used herein, the term "effective amount" or "pharmaceutically effective amount" or "therapeutically effective amount" or "prophylactically effective amount" of a composition, is a quantity sufficient to achieve a desired therapeutic and/or prophylactic effect, e.g., an amount which results in the prevention of, or a decrease in, the symptoms associated with a disease that is being treated, e.g., a cancer. The amount of a composition administered to the subject will depend on the type and severity of the disease and on the characteristics of the individual, such as general health, age, sex, body weight and tolerance to drugs. It will also depend on the degree, severity and type of disease. In some embodiments, an effective amount of an oncolytic virus may be administered to a subject having cancer in an amount sufficient to exert oncolytic activity, causing attenuation or inhibition of tumor cell proliferation leading to primary and/or metastatic tumor regression.

As used herein, the term "humanized" refers to forms of non-human (e.g., murine) antibodies that are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curro Op. Struct. Biol.* 2:593-596 (1992).

As used herein, the term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, etc.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567).

As used herein, the term "PD-1" is an acronym for the Programmed Cell Death 1 protein, a 50-55 kDa type I transmembrane receptor originally identified by subtractive hybridization of a mouse T cell line undergoing apoptosis (Ishida et al., 1992, *Embo J.* 11:3887-95). PD-1 is expressed on activated T, B, and myeloid lineage cells (Greenwald et al., 2005, *Annu. Rev. Immunol.* 23:515-48; Sharpe et al., 2007, *Nat. Immunol.* 8:239-45). The amino acid sequence of human PD-1 is GenBank Accession No. NP 005009.2. The amino acid sequence of murine PD-1 is GenBank Accession No. AAI19180.1.

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and doublestranded regions, single- and double-stranded RNA, RNA that is mixture of single- and double-stranded regions, and hybrid molecules comprising DNA and RNA that may be single-stranded or, more typically, double-stranded or a mixture of single- and doublestranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons. In a particular embodiment, the polynucleotide contains sequences encoding a PD-1 binding agent, such as an anti-PD-1 antibody (e.g., an anti-PD-1 scFv).

As used herein, the terms "polypeptide", "peptide" and "protein" are used interchangeably to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature. In a particular embodiment, the polypeptide contains polypeptide sequences of a PD-1 binding agent, such as an anti-PD-1 antibody (e.g., an anti-PD-1 scFv).

As used herein, the term "recombinant" when used with reference, e.g., to a cell, virus, nucleic acid, protein, or vector, indicates that the cell, virus, nucleic acid, protein or vector, has been modified by the introduction of a heterologous nucleic acid or protein or the alteration of a native nucleic acid or protein, or that the material is derived from a cell so modified. Thus, e.g., recombinant viruses express genes that are not found within the native (non-recombinant) form of the virus or express native genes that are otherwise abnormally expressed, under expressed or not expressed at all. Thus, when referring to a "recombinant HSV" or "recombinant vaccinia" it is meant that the HSV or vaccinia has been genetically altered, e.g., by the addition or insertion of a selected gene, e.g., a PD-1 binding agent.

As used herein, the term "subject" refers to an organism administered one or more active agents. Typically, the subject is a mammal, such as an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like). Typically, the terms "subject" and "patient" are used interchangeably herein in reference to a human subject.

As used herein, the terms "treating" or "treatment" or "alleviation" refers to both therapeutic treatment and prophylactic or preventative measures, wherein the object is to prevent or slow down (lessen) the targeted pathologic condition or disorder. For example, a subject is successfully "treated" for a cancer, if after receiving a therapeutic amount of the compositions described herein, the subject shows observable and/or measurable reduction in or absence of one or more signs and symptoms of the cancer, e.g., reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, of one or more of the symptoms associated with the specific cancer; reduced morbidity and mortality, and improvement in quality of life issues.

DETAILED DESCRIPTION OF THE INVENTION

The present invention is directed toward medicaments for inhibiting tumor growth and improving therapy in solid tumors and metastasis.

The invention provides a treatment of solid tumors comprising administering to a patient, an effective amount of an immune checkpoint inhibitor and an immune stimulating cytotoxic gene therapy. Tumor cells are transfected by direct injection of the gene delivery vehicle into accessible rumor lesions, followed by prodrug administration. Useful prodrugs include ganciclovir, acyclovir, valacyclovir, valgancyclovir, famciclovir or an active analog thereof. The local reaction includes tumor cell necrosis, liberation of tumor antigens. Unexpectedly the immune stimulating cytotoxic gene therapy induces or increases the presence of immune checkpoint molecules, including PD-L1, PD-L2 within the tumor.

The increased levels of immune checkpoint molecules in the tumor resulting from immune stimulating cytotoxic gene therapy enhances efficacy of immune checkpoint inhibitors such as antibodies that recognize CTLA4, PD-1, PD-L1, or PD-L2. Immune checkpoint inhibitors such as antibodies that recognize CTLA4, PD-1, PD-L1, or PD-L2 enhance the efficacy of immune stimulating cytotoxic gene therapy.

The use of cytotoxic gene therapy in combination with an immune checkpoint inhibitor is intended to enhance T-cell activation through different mechanisms, respectively augmenting T-cell activation and augmenting dendritic cell-mediated tumor antigen presentation (Kaufman et al., Ann Surg Oncol., 17(3):718-730, 2010) following the release of tumor antigens by the cytotoxic activity and antagonizing immune tolerance by blocking inhibitory signals mediated by a immune checkpoint inhibitor, such as CTLA-4 or PD-1 on T lymphocytes (Kapadia and Fong, J Clin Oncol., 23:8926-8928, 2005).

The result is an enhanced anti-tumor effect against both the injected tumor and non-injected tumors, including metastases. The combination of provides a cumulative effect that is greater than the expected additive effect for the agents individually.

The invention is intended to enhance the local anti-tumor response to tumor antigens following the cytotoxic activity in tumors, leading to a greater systemic protective effect. Therefore, the combination therapy may result in enhanced destruction of injected tumors as well as uninjected/distant tumors, including micrometastatic disease to improve the rate of overall tumor response and duration of response. Overall, these effects may contribute to an improvement in overall survival, particularly when compared to treatment using either agent alone.

Without wishing to be bound by any theory of the invention, in one embodiment the combination of a cytotoxic gene therapy and an immune checkpoint inhibitor may increase the frequency or intensity of tumor-specific T cell responses in treated patients as compared to either agent alone In another embodiment of this invention the combination of a cytotoxic gene therapy and an immune checkpoint inhibitor may result in reduction in cancer recurrences in treated patients, as compared to either agent alone.

In yet another embodiment of this invention the combination of a cytotoxic gene therapy and an immune checkpoint inhibitor may result in reduction of the presence or appearance of metastases or micro metastases in treated cancer patients, as compared to either agent alone.

In another embodiment of this invention the combination of a cytotoxic gene therapy and an immune checkpoint inhibitor may result improved overall survival of treated cancer patients, as compared to either agent alone.

As used herein, the term "immune checkpoint inhibitor" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD 80 and CD86; and PD-1 with its ligands PD-L1 and PD-L2 (Pardoll, Nature Reviews Cancer 12: 252-264, 2012). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies.

CTLA-4 is an immune checkpoint molecule that down-regulates pathways of T-cell activation. CTLA-4 is a negative regulator of T-cell activation. Blockade of CTLA-4 has been shown to augment T-cell activation and proliferation. The combination of the cytotoxic gene therapy and the anti-CTLA-4 antibody is intended to enhance T-cell activation through two different mechanisms in order to augment the anti-tumor immune response to tumor antigen released following the cytotoxic tumor lysis of the cytotoxic gene therapy in the tumor. Therefore, the combination of the cytotoxic gene therapy and the anti-CTLA-4 antibody may enhance the destruction of the injected and un-injected/distal tumors, improve overall tumor response, and extend overall survival, in particular where the extension of overall survival is compared to that obtained using an anti-CTLA-4 antibody alone.

PD-1 is an immune checkpoint molecule that down-regulates pathways of T-cell activation. PD-1 binds to PD-L1 and PD-L2. PD-1 is a negative regulator of T-cell activation. Blockade of PD-1 PD-L1/PD-L2 interactions have been shown to augment T-cell activation and proliferation. The combination of the cytotoxic gene therapy and the antibody against PD-1, PD-L1, or PL-L2 is intended to enhance T-cell activation through two different mechanisms in order to augment the anti-tumor immune response to tumor antigen released following the cytotoxic tumor lysis of the cytotoxic gene therapy in the tumor. Therefore, the combination of the cytotoxic gene therapy and the anti-PD-1 antibody may enhance the destruction of the injected and un-injected/distal tumors, improve overall tumor response, and extend overall survival, in particular where the extension of overall survival is compared to that obtained using an anti-PD-1 antibody alone.

Within another aspect of the present invention, GDV constructs resulting in the expression of the thymidine kinase or cytosine deaminase, are administered to a solid tumor in a patient at various doses In the case of AdV-tk the expected range is between $10^4$ and $10^{15}$ vector particles (vp). Titres of adenoviral vectors used in the clinic typically range between $10^8$ vp/ml and $10^{13}$ vp/ml. Patients can be injected with 0.3 ml to 500 ml of vector with single or repeated doses. The tumor lesion may vary from 1 to 20 cm in size, for example, in the case of soft tissue sarcoma, multiple myeoloma, or head and neck squamous cell carcinoma. The dose can be administered in a single injection or in multiple injections within the same tumor site over a time period. Alternatively, a dose consisting of up to 500 mls per day can be administered over a time period of 5 days in order to establish one course. Patients can receive as many courses as necessary in order to establish a response without proving toxic. Courses can be given, for example, weekly or every other week over months or over years.

As noted above, pharmaceutical compositions are described comprising a GDV carrying the thymidine kinase vector construct, in combination with a pharmaceutically acceptable carrier or diluent (see Nyberg-Hoffman and Aguilar-Cordova, Nature Medicine, April 1999). The composition may be prepared either as a liquid solution, or as a solid form (e.g., lyophilized), which is suspended in a solution prior to administration. In addition, the composition may be prepared with suitable carriers or diluents for surface administration, injection, oral, or rectal administration.

Pharmaceutically acceptable carriers or diluents are non-toxic to recipients at the dosages and concentrations employed. Representative examples of carriers or diluents for injectable solutions include water, isotonic saline solutions which are preferably buffered at a physiological pH or a pH for vector stability (such as phosphate-buffered saline or Tris-buffered saline), mannitol, dextrose, sucrose, glycerol, and ethanol, as well as polypeptides or proteins such as human serum albumin.

Various methods may be utilized within the context of the present invention in order to directly administer the vector construct to the tumor, including direct intra-lesional injection, intra-cavital, iv administration or topical delivery. For example, within one embodiment a lesion may be located, and the vector injected once or several times in several different locations within the body of the tumor. Alternatively, arteries or blood vessels, which serve a tumor, may be identified and the vector injected into such blood vessel, in order to deliver the vector directly into the tumor. Within another embodiment, a tumor that has a necrotic center may be aspirated, and the vector injected directly into the now empty center of the tumor. Within yet another embodiment, the vector construct may be directly administered to the surface of the tumor, for example, by application of a topical pharmaceutical composition containing the vector construct, or preferably, a recombinant viral vector carrying the vector construct. Vector particles may be administered either directly (e.g., intravenously, intramuscularly, intraperitoneally, subcutaneously, orally, rectally, intraocularly, intranasally, intravesically, during surgical intervention) to the site of a tumor lesion, or the vector construct may be delivered after formulation by various physical methods such as lipofection (Feigner et al., PNAS 84:_7413-7417, 1989), direct DNA injection (Fung et al., PNAS 80:_353-357, 1983; Seeger et al., PNAS 81:_5849-5852; Acsadi et al., Nature 352:_815-818, 1991); microprojectile bombardment (Williams et al., PNAS 88:_2726-2730, 1991); liposomes of several types (see, e.g., Wang et al., PNAS 84:_7851-7855, 1987); CaPO4 (Dubensky et al., PNAS 81:_7529-7533, 1984); DNA ligand (Wu et al., J. Biol. Chem. 264: 16985-16987, 1989); administration of nucleic acids alone (WO 90/11092); or administration of DNA linked to killed adenovirus (Curiel et al., Hum. Gene Ther. 3:_147-154, 1992); via polycation compounds such as polylysine, utilizing receptor specific ligands; as well as with psoralen inactivated viruses such as Sendai or Adenovirus, by electroporation or by pressure-mediated delivery. In addition vector particles or formulated construct may either be administered by direct injection to the desired site or by other clinically acceptable means such as by various forms of catheter that can be introduced into the patient with minimal discomfort, followed by injection or release of the vector in conjunction with operations made possible by the catheter, such as multiple injection, introduction of radioactive seeds, tissue disruption and other means known to those skilled in the art.

Vector particles and formulated vector constructs may be administered to a wide variety of tissue and/or cell types where lesions may exist, including for example, the brain and/or spinal cord, bone marrow, eyes, the liver, nose, throat and lung, heart and blood vessels, spleen, skin, circulation, muscles, prostate, breast, pancreas, kidney, cervix, and other organs.

Evaluation of Patients with Cancer

Every patient with any form of tumor is followed and staged in different ways depending on the tools and methods available and their accumulated track record in allowing reliable evaluation and effective disease management (for example see Medical Oncology: Basic Principles and Clinical Management of Cancer by Paul Calabresi, Philip S. Schein McGraw-Hill 1993, and Cancer, Principles and Practice of Oncology 5th edition, Vincent T. DeVita, Jr., Samuel Hellman and Steven A. Rosenberg Eds. Lippincott-Raven 1997)). For example, testicular cancer is followed with Beta HCG, AFP, and LDH, colon cancer is often followed with CEA levels, prostate cancer is followed with PSA levels, and ovarian cancer is followed with CA-125 levels. Tumors of the Head and Neck area, of the upper air and digestive tract are often followed by visual inspection as they are in an easy location to visualize. This is also the case for cervical cancer. Areas that are not easily visualized or palpated are evaluated with CT scans or MRI scans. MRI scans are extremely helpful in the evaluation of tumors of the neuraxis and the central nervous system. PET Scan is not routinely utilized to follow cancer. In the proceeding paragraphs prostate cancer is used as an example of the staging and treatment decisions of a solid tumor disease.

In one aspect, the technology provides methods for determining the efficacy cytoxic GDV and checkpoint inhibitor combination therapy for killing neoplastic cells and inducing a systemic immune response. There are many instances where it might be desirable to determine the efficacy of such a combination therapy. For example, it may be desirable to evaluate efficacy during the development of a new combination therapy. It may also be desirable to evaluate efficacy of a previously developed therapies to, for example, evaluate additional properties such as shelf life, production methods, etc.

In some embodiments, the methods involve measuring the efficacy of the combination therapy in vivo. For example, the tumor may be examined using classical imaging techniques (e.g., CT and PET) before and after treatment to determine the effects of the combination therapy.

In some embodiments, the invention will be used in combination with an adjuvant. In one embodiment, the adjuvant comprising a cytokine for enhancements of innate and adaptive immunity. The cytokine can be administered as a cytokine containing formulation or a GDV that will result in the expression of a cytokine upon administration to the patient.

In some embodiments, the invention involves contacting a cancer cell with the cytotoxic GDV and determining the viability of the cancer cell. Cell viability may be evaluated by anyone of a number of methods known in the art. For example, the viability may be evaluated in a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, and a nuclear fragmentation assay. It is understood that assays of cell viability are capable of detecting cell killing (i.e., cell death). Cell death may be, for example, cytolytic, apoptotic, or necrotic.

Other exemplary assays of cell viability include BrdU, EdU, or H3-Thymidine incorporation assays; DNA content assays using a nucleic acid dye, such as Hoechst Dye, DAPI, Actinomycin D, 7-aminoactinomycin D or Propidium Iodide; Cellular metabolism assays such as AlamarBlue, MTT, XTT, and CeliTitre Glo; Nuclear Fragmentation Assays; Cytoplasmic Histone Associated DNA Fragmentation Assay; PARP Cleavage Assay; TUNEL staining; and Annexin staining. Still other assays will be apparent to one of ordinary skill in the art.

The cancer cells used in the efficacy evaluation methods may be any of the cancer cell lines disclosed herein and/or known in the art. In certain cases, it is desirable that the cancer cell is of a specific type. For example, it is particularly desirable that the cancer cell is a pancreatic cell when the condition to be treated by the oncolytic virus under evaluation is a pancreatic cancer.

In some cases, evaluation methods involve determining the expression of a cancer cell marker (e.g., at least one) in the cancer cell. Any appropriate cancer cell biomarker may be used. The cancer cell biomarkers can be evaluated by any appropriate method known in the art. For example, immunoblotting, immunohistochemistry, immunocytochemistry, ELISA, radioimmunoassays, proteomics methods, such as mass spectroscopy or antibody arrays may be used. In some embodiments, high-content imaging or Fluorescence-activated cell sorting (FACS) of cells may be used. Other exemplary methods will be apparent to the skilled artisan.

Typically, the methods for determining the efficacy of cytotoxic GDV for killing cancer cells are carried out in vitro under standard cell culture conditions. However, the methods are not so limited. The methods may involve growing cancer cells and optionally control cells, which mayor may not be cancer cells. The cells may be grown in single well or multi-well format (e.g., 6, 12, 24, 96, 384, or 1536 well format). Thus, in some cases the assays may be adapted to a high-throughput format.

EXAMPLE 1

AdV-tk Mediated Gene Therapy in Combination with Checkpoint Inhibitors for the Treatment of Glioma One application of this invention would be in the treatments of malignant gliomas patients where a craniotomy with resection of the tumor or tumors will be performed. At the neurosurgeon's discretion, this may involve stereotactic methods and/or intraoperative navigational guidance and/or intraoperative MRI or other radiologic guidance. Tumor resection may be partial or complete. After the tumor resection has been completed, freehand injections of between 10-1000 microliters of the AdV-tk virus will be performed by the neurosurgeon in the wall of the resection cavity at a number of sites ranging from 1 to 50 to a total volume injected of between 100 microliters and 5000 microliters. The total dose of the AdV-tk may range between $1\times10^8$ to $1\times10^{12}$ vector particles. After the injections are completed, the remainder of the operation will consist of routine wound closure.

After completion of surgery, the patient will receive prodrug. In this example, Valacyclovir treatment will begin 1-3 days after vector administration at a dose of 2 grams orally three times a day for 14 days. Certain patients, such as those with impaired renal function, may receive a modified dose schedule such as 1.5 grams orally three times a day, or 1.5 grams twice a day. Alternatively, if a patient is unable to take the oral prodrug for any reason, intravenous acyclovir at 10 mg/kg tid may be substituted.

In this example, administration of an immune checkpoint inhibitor antibody such as pembrolizumab (anti-PD-1) will then be initiated within 1-21 days after surgery. Intravenous dosing will be approximately 1-4 mg/kg once every two or three weeks.

Clinical patient outcomes will be monitored using standard methodology, including tumor progression, quality of life, blood chemistry, immune system status, general wellness, and survival.

In this example, the patients receiving the combination treatment will have improved outcomes when compared to patents with similar disease characteristics that receive current standard of care or either single agent alone. Improvements in outcomes may include improved survival time post-treatment, increased time to disease recurrence, and better quality of life.

EXAMPLE 2

AdV-tk Mediated Gene Therapy in Combination with Checkpoint Inhibitors for the Treatment of Pancreatic Adenocarcinoma Another application of this invention would be in the treatment of patients with pancreatic adenocarcinoma. In this example, two courses of AdV-tk+prodrug will be delivered. Prior to the first injection, pathologic diagnosis of pancreatic adenocarcinoma will be made. For the injections that performed before surgery or injections to patents not receiving surgery, between $3\times10^{10}$ and $1\times10^{12}$ vector particles of AdV-tk will be delivered by Endoscopic Ultrasound or CT-guided injection into the pancreas in a total volume in the range of 0.5 mls to 4 mls. For patients receiving surgery, freehand injections, each of a volume of between 10 and 1000 microliters of the AdV-tk vector formulation, will be performed by the surgeon into each of between and 2-20 sites into the soft tissue of the retroperitoneum or to any residual macroscopic tumor. The total dose of the AdV-tk will be between $3\times10^{10}$ and $1\times10^{12}$ vector particles in a total volume in the range of 1 ml to 5 ml. The sites will be at least 1 cm apart and will be selected by the surgeon to avoid injections into vessels, bowel or other critical structures.

After the completion of each course, the patient will receive prodrug. In this example, Valacyclovir treatment will begin 1-3 days after vector administration at a dose of 2 grams orally three times a day for 14 days. Certain patients, such as those with impaired renal function, may receive a modified dose schedule such as 1.5 grams orally three times a day, or 1.5 grams twice a day. Alternatively, if a patient is unable to take the oral prodrug for any reason, intravenous acyclovir at 10 mg/kg tid may be substituted.

In this example, administration of an immune checkpoint inhibitor antibody such as Ipilimumab (anti-CTLA-4) will then be initiated within 1-21 days after surgery. Intravenous dosing will be approximately 1-4 mg/kg once every two or three weeks.

Clinical patient outcomes will be monitored using standard methodology, including tumor progression, quality of life, blood chemistry, immune system status, general wellness, and survival.

In this example, the patients receiving the combination treatment will have improved outcomes when compared to patents with similar disease characteristics that receive current standard of care or either single agent alone. Improvements in outcomes may include improved survival time post-treatment, increased time to disease recurrence, and better quality of life.

EXAMPLE 3

AdV-tk Mediated Gene Therapy in Combination with Checkpoint Inhibitors for the Treatment of Malignant Pleural Effusion Yet another application of this invention would be in the treatment of patients with malignant pleural effusions. Eligible patients will be seen by the interventional pulmonologists for placement of pleural catheter as per current standard of care. The cytotoxic gene therapy, such as AdV-tk vector in this case, will be delivered to the pleural space through the pleurex catheter after drainage of any fluids. For AdV-tk cytotoxic gene therapy, between $1\times10^{12}$ and $1\times10^{13}$ vector particles will be delivered in a total volume in the range of 10 mls and 50 mls. After a period of time within the range of 5 minutes and 60 minutes, the pleural cavity will be drained. A second infusion may be administered between 1-5 days after the first infusion.

After completion of infusions, the patient will receive prodrug. In this example, Valacyclovir treatment will begin 1-3 days after vector administration at a dose of 2 grams orally three times a day for 14 days. Certain patients, such as those with impaired renal function, may receive a modified dose schedule such as 1.5 grams orally three times a day, or 1.5 grams twice a day. Alternatively, if a patient is unable to take the oral prodrug for any reason, intravenous acyclovir at 10 mg/kg tid may be substituted.

In this example, administration of an immune checkpoint inhibitor antibody such as lambrolizumab (anti-PD-1) will then be initiated within 1-21 days after surgery. Intravenous dosing will be approximately 1-4 mg/kg once every two or three weeks.

Clinical patient outcomes will be monitored using standard methodology, including tumor progression, quality of life, blood chemistry, immune system status, general wellness, and survival.

In this example, the patients receiving the combination treatment will have improved outcomes when compared to patents with similar disease characteristics that receive current standard of care or either single agent alone. Improvements in outcomes may include improved survival time post-treatment, increased time to disease recurrence, and better quality of life.

FIG. 1 Induction of PD-L1 in Human Glioma Cells Response to Cytotoxic Gene Therapy.

FIG. 1 shows a time course of PD-L1/PD-L2 expression levels in human glioma (U251) cells in culture after treatment with cytotoxic gene therapy. The effect of AdV-tk/ prodrug cytotoxicity on the expression of immune checkpoint proteins (PD-1, PD-L1, PD-L2, CTLA-4, CD80, CD86) was tested by quantitative PCR. A substantial induction of gene expression relative to GAPDH mRNA observed with each checkpoint protein. The induction expression indicates that the AdV-tk/prodrug induced immunogenicity would be potentiated by inhibition of checkpoint blockade.

Figure 2:
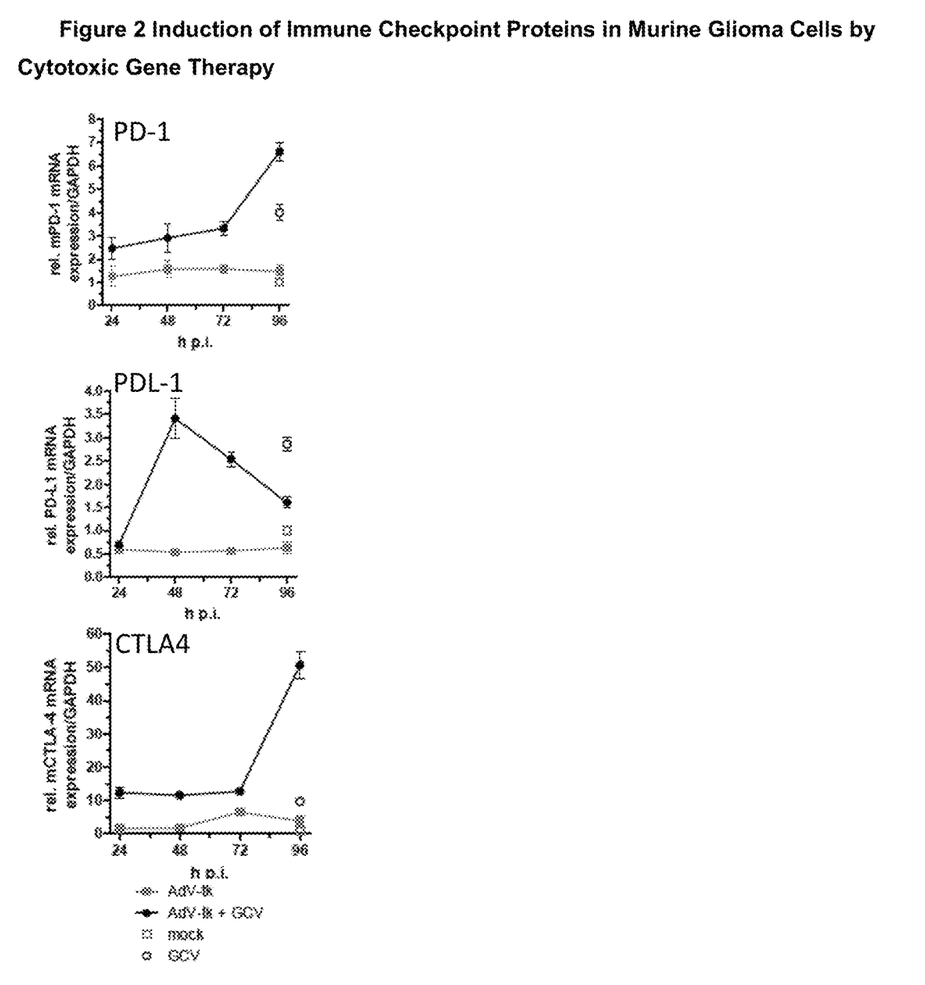

FIG. 2 Induction of PD-L1 in Glioma Cells Response to Cytotoxic Gene Therapy

FIG. 2 shows a time course of PD-L1/PD-L2 expression levels in murine glioma cells (GL-261) in culture after treatment with cytotoxic gene therapy. The effect of AdV-tk/prodrug cytotoxicity on the expression of immune checkpoint ligands (PD-L1, PD-L2) was tested by quantitative PCR. A substantial induction of gene expression relative to GAPDH mRNA observed with each PD-L1 and PD-L2. The induction of PD-L1/PD-L2 expression indicates that the AdV-tk induced immunogenicity would be potentiated by inhibition of checkpoint blockade.

Figure 3:
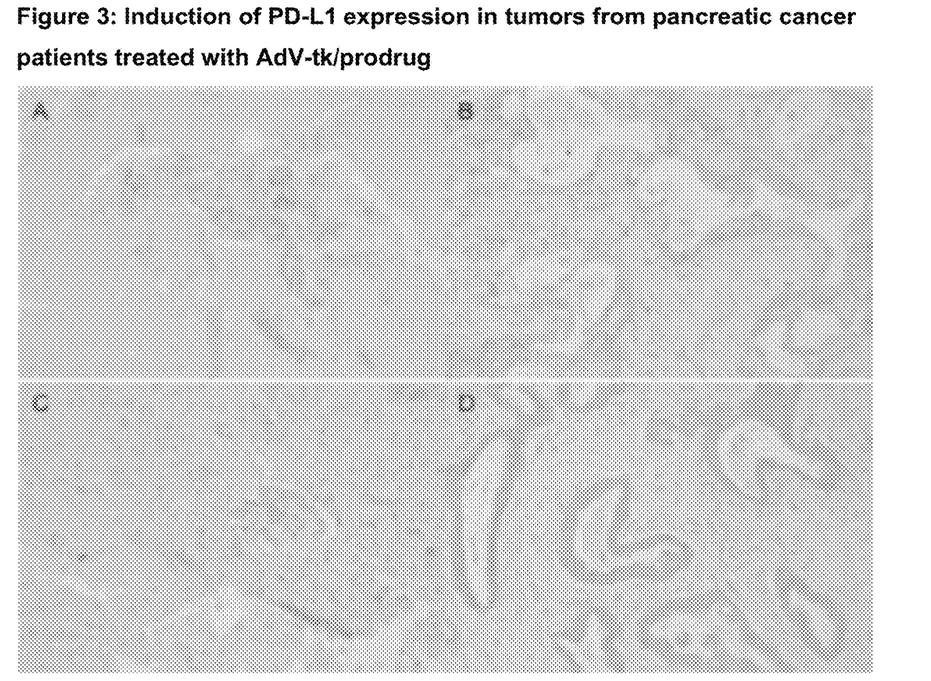

FIG. 3 Induction of PD-L1 Expression in Tumor Tissue from Pancreatic Cancer Patients in Response to AdV-tk/Prodrug.

PD-L1 expression was characterized in resected tumors after AdV-tk/prodrug treatment and compared to pre-treatment fine needle aspirate samples from a study of AdV-tk in pancreatic cancer. All samples analyzed had an average fold increase of 21.66 (range 6.00-74.85, p=0.0021) in CD8+ T cell infiltrate; with CD4+ infiltrates not significantly altered. PDL1 expression levels were increased in 5 of 7 samples analyzed. These data further support the combined use of AdV-tk immune-stimulation with ICI of the PD1/PD-L1 axis. Two examples are shown: before (A, C) and after (B, D) AdV-tk injection and 14 days of valacyclovir; Paraffin sections from pretreatment fine needle aspirate (A and C) or post-treatment surgical resection (B and D) were stained with the anti-PD-L1 antibody.

The invention claimed is:

1. A method of decreasing tumor burden in a mammal comprising:
   i) administering a replication-incompetent adenoviral vector encoding thymidine kinase to a mammal with a tumor intratumorally;
   ii) administering a prodrug to the mammal orally or intravenously, wherein the prodrug is ganciclovir, acyclovir, valacyclovir, valgancyclovir, famiciclovir, or an active analog thereof, such that the prodrug is activated by the thymidine kinase; and
   iii) administering a monoclonal antibody that recognizes the checkpoint protein PD1 to the mammal intravenously such that the antibody reduces the immune repressive response caused by the checkpoint protein, thereby allowing enhanced T cell activation,
   wherein the activated prodrug and enhanced T cell activation decrease tumor burden.

2. The method of claim 1, wherein the cancer is a colon, prostate, breast, lung, skin, liver, bone, pancreas, ovary, testis, bladder, kidney, brain, head, or neck cancer.

3. The method of claim 1, wherein the vector in the composition comprises a nucleic acid sequence encoding an interferon, a colony stimulating factor, an interleukin, a chemokine, a cytokine, or a costimulatory protein.

4. The method of claim 1, further comprising administering radiotherapy and or surgery to the mammal before, during, or following administering the vector, prodrug, and monoclonal antibody.

5. The method of claim 1, wherein the prodrug is valacyclovir.

6. A method of treating a mammal with a tumor resection comprising:
   i) administering a replication-incompetent adenoviral vector encoding thymidine kinase to a tumor resection site in a mammal;
   ii) administering a prodrug to the mammal orally or intravenously, wherein the prodrug is ganciclovir, acyclovir, valacyclovir, valgancyclovir, famiciclovir, or an active analog thereof, such that the prodrug is activated by the thymidine kinase; and
   iii) administering a monoclonal antibody that recognizes the checkpoint protein PD1 to the mammal intravenously such that the antibody reduces the immune repressive response caused by the checkpoint protein, thereby allowing enhanced T cell activation,
   wherein the activated prodrug and enhanced T cell activation decrease micrometastases.

* * * * *